(12) United States Patent
Azria et al.

(10) Patent No.: US 9,622,975 B2
(45) Date of Patent: Apr. 18, 2017

(54) PHARMACEUTICAL COMPOSITION

(71) Applicant: Novartis AG, Basel (CH)

(72) Inventors: Moise Azria, Basel (CH); Simon David Bateman, Randolph, NJ (US); Anasuya Ashok Ghosh, Basking Ridge, NJ (US); Shoufeng Li, Basking Ridge, NJ (US); Alan Edward Royce, Saylorsburg, PA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/718,595

(22) Filed: May 21, 2015

(65) Prior Publication Data
US 2015/0250729 A1 Sep. 10, 2015

Related U.S. Application Data

(60) Continuation of application No. 13/079,400, filed on Apr. 4, 2011, now abandoned, which is a division of application No. 12/093,383, filed as application No. PCT/US2006/044642 on Nov. 16, 2006, now abandoned.

(60) Provisional application No. 60/737,631, filed on Nov. 17, 2005.

(51) Int. Cl.
| | |
|---|---|
| *A61K 38/29* | (2006.01) |
| *A61K 9/20* | (2006.01) |
| *A61K 31/198* | (2006.01) |
| *A61K 38/23* | (2006.01) |

(52) U.S. Cl.
CPC .......... *A61K 9/2013* (2013.01); *A61K 9/2027* (2013.01); *A61K 9/2054* (2013.01); *A61K 9/2095* (2013.01); *A61K 31/198* (2013.01); *A61K 38/23* (2013.01); *A61K 38/29* (2013.01)

(58) Field of Classification Search
CPC ..................................................... A61K 38/29
USPC ........................................................ 514/11.8
See application file for complete search history.

(56) References Cited

U.S. PATENT DOCUMENTS

| | | | |
|---|---|---|---|
| 4,159,345 | A | 6/1979 | Takeo et al. |
| 4,755,385 | A | 7/1988 | Etienne et al. |
| 5,096,714 | A | 3/1992 | Kuhrts |
| 5,213,806 | A | 5/1993 | Ito et al. |
| 5,948,422 | A | 9/1999 | Van Koutrik et al. |
| 6,361,794 | B1 | 3/2002 | Kushia et al. |
| 2002/0123459 | A1 | 9/2002 | Ault et al. |
| 2005/0186267 | A1 | 8/2005 | Thompson et al. |

FOREIGN PATENT DOCUMENTS

| | | |
|---|---|---|
| CN | 1479612 | 3/2004 |
| WO | 02/045754 | 6/2002 |
| WO | 2005/014031 | 2/2005 |
| WO | 2006/040114 | 4/2006 |

OTHER PUBLICATIONS

Kahn K.A., The Journal of Pharmacy and Pharmacology 28(8), 633-636 (1976).
Gordon M.S., Journal of Pharmaceutical Sciences 76(12), 907-909 (1987).
Johnson J.R., Journal of Pharmaceutical Sciences 80(5), 469-71 (1991).
Marshall P.V., Journal of Pharmaceutical Sciences 80(9), 899-903 (1991).

*Primary Examiner* — David Lukton
(74) *Attorney, Agent, or Firm* — Pokalsky Wilczynski Brozek, LLP

(57) ABSTRACT

The present invention provides oral pharmaceutical compositions that enable the successful delivery of drugs in a pharmaceutically effective amount, particularly poly (amino acids) such as peptides, peptidomimetics and proteins. e.g. hormones to a subject via oral administration to accomplish the desired therapeutic effect. The oral pharmaceutical composition comprising a poly (amino acid) as the active ingredient, e.g. a peptide or protein, shows a rapid disintegration and/or dissolution such that the active ingredient is able to attain a therapeutic effect.

8 Claims, 7 Drawing Sheets

Figure 1: Dissolution of formulation with more lubrication

Figure 2: Dissolution of formulation with less lubrication

Figure 3: The effect of tablet hardness on disintegration time (DT) in minutes

Pilot batches tested in Monkeys

PHARMACEUTICAL COMPOSITION

This application is a continuation of U.S. patent application Ser. No. 13/079,400, filed Apr. 4, 2011, abandoned; which is a divisional of U.S. patent application Ser. No. 12/093,383, filed May 12, 2008, abandoned; which is a 371 of PCT/US06/44642, filed Nov. 16, 2006; which claims benefit of U.S. Provisional Application No. 60/737,631, filed Nov. 17, 2005; which in its entirety is herein incorporated by reference.

The present invention relates to a novel pharmaceutical composition for the oral delivery of pharmaceutical compounds, in particular poly(amino acids) including peptides or, alternatively, peptidomimetics.

In particular, the present invention relates in an embodiment to a novel oral pharmaceutical composition containing a poly(amino acid), for the treatment of a disorder caused by abnormal bone resorption and/or to the treatment of an arthritic condition and to other subject matter.

BACKGROUND TO THE INVENTION

Hormones

Poly(amino acids) which have been used or proposed to be used for pharmaceutical or veterinary purposes include, but are not limited to the following, including synthetic, natural or recombinant sources thereof: polypeptide hormones such as calcitonins, e.g. salmon calcitonin, growth hormone, including human growth hormones (hGH), recombinant human growth hormones (rhGH), bovine growth hormones, and porcine growth hormones; growth hormone-releasing hormones and pituitary thyroid hormone.

The parathyroid hormone or PTH can be the full length, 84 amino acid form of parathyroid hormone, e.g. the human form, hPTH (1-84), or any polypeptide, protein, protein fragment, or modified fragment, i.e. PTH-related peptides and PTH analogs, capable of mimicking the activity of hPTH (1-84) in controlling calcium and phosphate metabolism to build bone in the human body. The PTH fragments will generally incorporate at least the first 28 N-terminal residue and include by way of example PTH (1-28), PTH (1-31), PTH (1-34), PTH (1-37), PTH (1-38) and PTH (1-41) and analogues thereof, e.g. PTS893. The PTH can be a single PTH or any combination of two or more PTHs.

The preferred PTH fragment is PTH (1-34).

These parathyroid hormones are commercially available or can be obtained recombinantly, by peptide synthesis, or by extraction from human fluid by methods well established in the art.

The amount of PTH to be administered is generally an amount effective to stimulate new bone formation i.e. a therapeutically effective amount. This amount will necessarily vary with the age, size, sex and condition of the subject to be treated, the nature and severity of the disorder to be treated and the like. However, the unit amount can be less than the described dosage when a plurality of the compositions are to be administered, i.e., the total effective amount can be administered in cumulative dosage units. The unit amount of PTH can also be more than the effective amount when the composition provides sustained release of the pharmacologically active agent. The total amount of PTH to be used can be determined by methods known to those skilled in the art. However, in general, satisfactory results will be obtained systemically at daily dosages of from about 0.001 µg/kg to about 10 mg/kg animal body weight, preferably 1 µg/kg to about 6 µg/kg body weight.

The preferred pharmacologically active agent is a pharmacologically active peptide, particularly calcitonin. A known class of pharmacologically active agents, calcitonins have varying pharmaceutical utility and are commonly employed in the treatment of e.g. Paget's disease, hypercalcemia and postmenopausal osteoporosis. Calcitonins, e.g. salmon, (Asu1-7)-eel or human calcitonin, are compounds which are long-chain polypeptide hormones secreted by the parafollicular cells of the thyroid gland in mammals and by the ultimobranchial gland of birds and fish. Various calcitonins, including salmon, pig and eel calcitonin are commercially available and commonly employed for the treatment of e.g. Paget's disease, hypercalcemia of malignancy and osteoporosis. The calcitonin can be any calcitonin, including natural, synthetic or recombinant sources thereof, as well as calcitonin derivatives such as 1,7-Asu-eel calcitonin. The compositions can comprise a single calcitonin or any combination of two or more calcitonins. The preferred calcitonin is synthetic salmon calcitonin.

The calcitonins are commercially available or may be synthesized by known methods.

The amount of pharmacologically active agent is generally an amount effective to accomplish the intended purpose, e.g. a therapeutically effective amount. However, the unit amount can be less than the described dosage when a plurality of the compositions are to be administered, i.e., the total effective amount can be administered in cumulative dosage units. The unit amount of active agent can also be more than the effective amount when the composition provides sustained release of the pharmacologically active agent. The total amount of active agent to be used can be determined by methods known to those skilled in the art. However, because the compositions may deliver the active agent more efficiently than prior compositions, less amounts of active agent than those used in prior dosage unit forms or delivery systems can be administered to a subject while still achieving the same blood levels and/or therapeutic effects.

The appropriate dosage of calcitonin to be administered will, of course, vary depending upon, for example, the amount of calcitonin to be administered and the severity of the condition being treated. However, in general, satisfactory results will be obtained through systemic intranasal or injectable administration at daily dosages of from about 0.5 µg/kg to about 10 µg/kg animal body weight, preferably 1 µg/kg to about 6 µg/kg body weight.

Human Growth Hormone (hGH) (or somatotropic hormone or somatotropin) is a polypeptide hormone secreted by the anterior lobe of the pituitary gland that promotes growth of the body, especially by stimulating release of somatomedin, and that influences the metabolism of proteins, carbohydrates, and lipids.

Included under the hGH definition may also be any of various natural or synthetic substances that regulate the growth of animals or plants, such as pituitary growth hormone in vertebrates and auxins in plants.

Bone Disorders

Many types of bone disorders are known. A first class of disorders fall in the class relating to disorders caused by bone resorption. Examples of such disorders are osteoporosis, osteolyisis and Paget's disease.

In a second class of disorders are arthritic conditions. An example of such disorders is osteoarthritis.

New Formulations

There have been many attempts to promote absorption of poly (amino acids) such as peptide and proteins, e.g. hormones. It is generally believed that peptides and proteins need to be protected from the gastric and intestinal environment, where many peptidases exist and significant degradation may occur. Enteric coating and the addition of peptidase inhibitors to pharmaceutical compositions have proven to be effective in improving poly(amino acid), e.g. protein and peptide, absorption via oral administration.

However, those approaches alone do not offer sufficient protection to achieve a satisfactory plasma level of the peptide and proteins, there still remains a need to provide alternative means for successfully delivering peptide and protein medicaments to a patient, whilst protecting them from chemical and enzymatic degradation in order to enable them to provide a therapeutic effect.

This is particularly the case for calcitonins, where oral administration is the preferred delivery route since it is convenient, relatively easy and generally painless, resulting in greater patient compliance relative to other modes of delivery.

SUMMARY OF THE INVENTION

Figure 1:
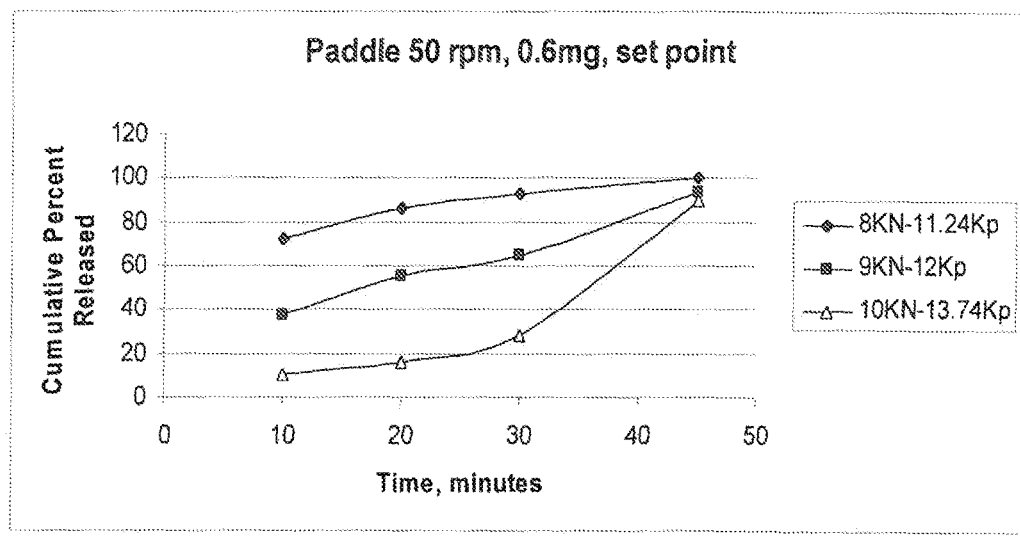
FIG. 1 is a graph illustrating the dissolution of formulation with more lubrication over time.
Figure 2:
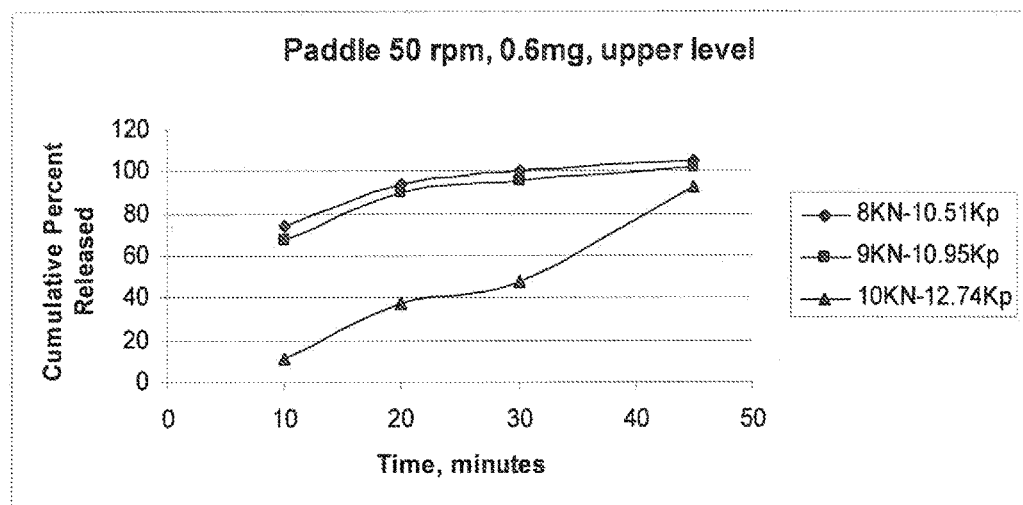
FIG. 2 is a graph illustrating the dissolution of formulation with less lubrication over time.

The present invention therefore provides a pharmaceutical composition that enables the successful delivery of drugs in a pharmaceutically effective amount, particularly poly (amino acids) such as peptides, peptidomimetics and proteins, e.g. hormones to a subject via oral administration to accomplish the desired therapeutic effect.

The present invention further provides an oral pharmaceutical composition comprising a poly (amino acid) active ingredient, e.g. a peptide or protein, in which the disintegration time of the pharmaceutical composition and/or the rate of dissolution are rapid such that the active ingredient is able to attain a therapeutic effect.

In a particular aspect, the present invention provides pharmaceutical compositions comprising a peptide or protein active ingredient in which the disintegration time of the pharmaceutical composition, e.g. tablet, is up to ten minutes.

The present invention also provides a pharmaceutical composition, e.g. tablet or capsule that has a dissolution time of up to thirty minutes, for example up to twenty minutes, usually up to ten minutes.

In particular, the present invention provides pharmaceutical compositions comprising a calcitonin as the active ingredient together with the delivery agent 5-CNAC, where the pharmaceutical composition is manufactured in such a way so as to provide improved oral bioavailability, e.g. satisfactory or optimal oral bioavailability for the calcitonin active ingredient.

By "Bioavailability" is to be understood within the scope of the present invention the percent of dose entering the systemic circulation after administration of a given dosage form. More explicitly, the ratio of the amount of drug "absorbed" from a test formulation to the amount "absorbed" after administration of a standard formulation. Frequently, the "standard formulation" used in assessing bioavailability is the aqueous solution of the drug, given intravenously.

The amount of drug absorbed is taken as a measure of the ability of the formulation to deliver drug to the sites of drug action; which depends on the disintegration and dissolution properties of the dosage form, and the rate of biotransformation relative to rate of absorption.

Dosage forms containing identical amounts of active drug may differ markedly in their abilities to make drug available, and therefore, in their abilities to permit the drug to manifest it's expected pharmacodynamic and therapeutic properties.

It was within the scope of the present invention that it has surprisingly been found that faster disintegration of the pharmaceutical compositions of the present invention in a subject, e.g. the stomach, provides the best absorption characteristics for the active peptides and proteins, where major peptide or protein degradation occurs by pepsin or other enzymes.

The present invention thus further provides a pharmaceutical composition capable of delivering a peptide or protein via oral administration without the need for an enteric coating or a peptidase inhibitor. In embodiments, therefore, the compositions of the invention are free of enteric coating or peptidase inhibitors, or both.

The calcitonin-containing pharmaceutical compositions of the present invention may be used to treat disorders relating to abnormal bone resorption or to treat arthritic conditions, as described herein.

In one embodiment, the invention relates to an oral pharmaceutical composition in the solid phase comprising:
  i. a poly(amino acid);
  ii. a delivery agent; and, optionally,
  iii. a diluent;
    wherein the composition has a disintegration time of no more than 10 minutes and a dissolution of >80% at 20 minutes, particularly a disintegration time of no more than 6 minutes and a dissolution of >90% at 20 minutes.

In particular, the composition according to the invention has a disintegration time of no more than 2 minutes.

In another embodiment, the composition according to the invention additionally comprises a disintegrant, particularly a disintegrant selected from any superdisintegrant, such as a crospovidone or a povidone and/or another agent that decreases disintegration time, for example by effervescent and/or other means.

In still another embodiment of the invention, a pharmaceutical composition is provided having a dissolution time of >80% at no more than 20 minutes in gastric media.

The invention further relates to a pharmaceutical composition which is in form of a tablet, particularly a compressed tablet, wherein the tablet has a hardness of between 3 Kp and 20 Kp, particularly of between 5 Kp and 15 Kp, more particularly of between 5 Kp and 7 Kp.

In a specific embodiment, the composition according to the invention comprises a polypeptide hormone, particularly a calcitonin, more particularly a salmon calcitonin.

In particular, the calcitonin is present in a therapeutically effective amount in free or salt form that provides a peak plasma concentration ($C_{max}$) of no less than 400 pg/mL, particularly no less than 800 pg/mL, more particularly no less than 1000 pg/mL, and/or a reduction in plasma calcium level of >20% in 6 hours in primate animal models, in particular monkeys.

In another embodiment of the invention, a composition is provided comprising a therapeutically effective amount of a calcitonin in free or salt form in a dosage range of between 0.15 mg and 2.5 mg, particularly of between 0.15 mg and 0.4 mg.

The composition according to the invention may further comprise the delivery agent 5-CNAC and/or crospovidone and/or povidone as a disintegrant. Additionally the composition may comprise one or more of a thickening agent, a stabilizer and a dry binder.

In one embodiment of the invention, the pharmaceutical composition is provided in form of a tablet, which has a weight of 500 mg.

In a specific embodiment of the invention, a pharmaceutical composition is provided comprising:

| | | |
|---|---|---|
| a. | Salmon calcitonin | 0.03 to 0.5 wt % |
| b. | Micronized 5-CNAC | 5 to 80 wt % |
| c. | Avicel PH 102 or 101 | 0 to 70 wt % |
| d. | Crospovidone, NF | 0 to 10% |
| e. | Magnesium stearate | 0 to 1.5 wt % |
| f. | Cab-o-sil | 0 to 1.5% | where the total percentages add up to 100.

Further provided is a pharmaceutical combination comprising
 a. the composition according to the invention and as described herein before, and
 b. a co-agent which is a bone resorption inhibitor, or a cathepsin K inhibitor.

In still another embodiment, a method of manufacturing an oral pharmaceutical composition is provided comprising the steps
 a. blending a poly(amino acid), a carrier and a disintegrant to make a first blend;
 b. optionally blending a dry binder to the first blend to make a second blend;
 c. optionally blending a stabilizer to the second blend to make a third blend;
 d. compressing the third blend into a tablet having a hardness of 5 Kp to 20 Kp.

In still another embodiment, the invention relates to the use of the pharmaceutical composition according to the invention and as described herein before for the manufacture of a medicament for the treatment of a disease caused by abnormal bone resorption such as, for example, osteoporosis, an arthritic disease, or osteoarthritis.

The invention further relates to a method of determining the absorption properties of a composition according to the invention and as described herein before comprising
 a. determining the dispersion time
 b. correlating the dispersion time to the dissolution time In another embodiment, the invention relates to a method of pre-determining peak plasma concentration ($C_{max}$) of an active ingredient in a patient to be treated with an oral pharmaceutical composition comprising said active ingredient, particularly calcitonin, more particularly salmon calcitonin, and a delivery agent which method comprises adjusting the disintegration time of the pharmaceutical composition and/or the dissolution time of the active ingredient such as to provide a favorable microenvironment in the gastro intestinal tract for the dissolution of the active ingredient in the intestine in order to optimize absorption of the active ingredient and to achieve a therapeutically effective peak plasma concentration of the active ingredient in the blood plasma, in particular a peak plasma concentration of no less than 400 pg/mL.

In particular, the favorable microenvironment in the gastro intestinal tract for the dissolution of the active ingredient in the intestine may be provided by the addition of 5-CNAC to the composition.

In a specific embodiment, a method of pre-determining peak plasma concentration (Cm) of an active ingredient in a patient to be treated with an oral pharmaceutical composition is provided, wherein the oral pharmaceutical composition is provided in form of a tablet and the disintegration time is adjusted by adapting the hardness of the tablet, particularly a tablet the hardness of which is in a range of between 3 Kp and 20 Kp and/or wherein the disintegration time is less than 10 min, particularly less than 1 min.

In still another embodiment, the invention relates to the use, to manufacture an oral pharmaceutical composition having a disintegration time and/or a dissolution time of not more than 10 minutes, of:
 (i) a poly(amino acid);
 (ii) a delivery agent; and
 (iii) a disintegrant.

In particular, 5-CNAC may be used to provide a favorable microenvironment in the gastro intestinal tract for the dissolution of salmon calcitonin.

DETAILED DESCRIPTION OF THE INVENTION

The present invention provides an oral pharmaceutical composition comprising a poly (amino acid) active ingredient e.g. a peptide or a protein, in which the disintegration time of the pharmaceutical composition is such that the active ingredient is able to attain an adequate therapeutic effect.

The present invention further provides an oral pharmaceutical composition comprising a poly (amino acid) active ingredient e.g. a peptide or a protein, in which the rate of dissolution of the pharmaceutical composition is such that the active ingredient is able to attain an adequate therapeutic effect.

The present invention further provides an oral pharmaceutical composition comprising a poly (amino acid) active ingredient e.g. a peptide or a protein, in which both the disintegration time and the rate of dissolution of the pharmaceutical composition are such that the active ingredient is able to attain an adequate therapeutic effect.

Considering that the rate of degradation is very fast, i.e occurs in milli seconds, it was believed that this rapid degradation cannot be compensated by ways of dissolution. However, it was surprisingly found within the scope of the present invention that sufficiently high a therapeutic level of active ingredient can be achieved in a relatively rapid time frame which is able to compensate the biochemical degradation (e.g. in the gastrointestinal tract) of the active ingredient.

As a result of increased plasma concentration of the therapeutically active ingredients, it will be appreciated that the compositions of the present invention may not require as much active ingredient to be present compared to compositions without the properties of the compositions described herein. This will, of course, not only have the benefit of reducing production costs of the resulting medicinal products but also reduced the risk of forming unwanted, or even toxic, metabolites of the active ingredient in the patient.

In addition, the compositions of the present invention may provide a method whereby the therapeutic level of an active ingredient, e.g. the plasma concentration of an active ingredient, may be controlled. In other words, where there is a linear, or near linear relationship between disintegration, dissolution and/or plasma concentration of an active ingredient, the desired plasma concentration in any given time may be predetermined by choosing a particular composition with a particular disintegration time and/or a particular dissolution time.

To this end, the present invention also includes a library of compositions, each having different disintegration and/or dissolution properties by ways as herein described. One particular library of compositions comprises a library of tablets, each having different a hardness, e.g. from 3 Kp to 20 Kp, particularly from 5 Kp to 20 Kp, more particularly from 5 Kp to 15 Kp, but especially from 5 Kp to 7 Kp. In a sub-library, each tablet of each hardness may also differ in the amount of active ingredient, carrier, diluent, lubricant, glidant or disintegrant, for example.

The current invention also includes a library of compositions, where the absence of lubricant may contribute to a faster onset of disintegration and dissolution.

In one aspect, the present invention provides an oral pharmaceutical composition that has one or both of a dissolution time or disintegration time of up to ten minutes.

The present invention provides compositions for which the degree of dissolution is between 20% and 100% using USP II paddle method in 0.1N HCl and 0.01% Tween-80 dissolution media over a prescribed period of time.

In particular, the compositions of the invention have a degree of dissolution of between 20% and 100%, e.g. 20%, 30%, 40%, 50%, 60%, 70%, 80%, 90% and 100% over a period of 0 to 60 minutes, for example 0, 1, 2, 3, 4, 5, 6, 7, 8, 9, 10, 11, 12, 13, 14, 15, 16, 17, 18, 19, 20, 25, 30, 35, 40, 45, 50, 55 and 60 minutes.

In a preferred aspect of the present invention, the dissolution times and degree of dissolution, as mentioned above, correlate to compositions having a disintegration time of less than ten minutes.

In one embodiment of the invention, the composition has a disintegration time of no more than 10 minutes and a dissolution of >80% at no more than 20 minutes, particularly a disintegration time of no more than 6 minutes and a dissolution of >90% at no more than 20 minutes, particularly in gastric media.

In still another embodiment, the composition has a disintegration time of no more than 10 minutes and a dissolution of >80% at 20 minutes, particularly a disintegration time of no more than 6 minutes and a dissolution of >90% at 20 minutes, particularly in gastric media.

The skilled person will be aware that a number of different parameters influence disintegration time or dissolution time of a solid phase oral formulation including:
  Dosage form (e.g. capsule or tablet)
  Identity of active agent
  Identity of additional ingredients, e.g. delivery agent, disintegrant, glidant, lubricant, diluent
  Amounts (ratios) of the ingredients
  Particle sizes
  Tablet hardness Therefore, it is not possible to set forth a universal set of parameters defining all compositions which have a specified disintegration and/or dissolution time but excluded all other compositions. Nonetheless, the skilled man has the appropriate knowledge and skills to make compositions having the dissolution time and the disintegration time disclosed herein. For the avoidance of doubt, this specification includes guidance as to the achievement and measurement of disintegration time and dissolution time.

The dissolution time of a compound may directly effect the plasma concentration of an active ingredient at any given time.

The present invention therefore includes a pharmaceutical composition in the solid phase comprising:
a poly(amino acid);
a delivery agent; and
if necessary a diluent;
wherein the composition has a disintegration time of no more than 10 minutes.

In particular, the present invention includes:
a pharmaceutical composition for the oral delivery of poly (amino acids) comprising
(i) a poly(amino acid)
(ii) a delivery agent
(iii) a diluent
wherein the composition has a dissolution time of no more than 10 minutes.

The present invention also includes:
a solid pharmaceutical composition for the oral delivery of poly(amino acids) comprising
(i) a poly(amino acid)
(ii) a delivery agent
(iii) a disintegrant
(iv) a diluent
wherein the composition has a disintegration time of no more than 10 minutes.

The solid composition may be in the form of a tablet. The tablet may be compressed in a manner as described herein.

The poly(amino acid) may be any poly(amino-acid) drug, e.g. comprising a protein or protein fragment. It may be any poly (amino acid) described above under the heading "Background to the Invention". In a particular class of pharmaceutical compositions, the poly(amino acid) is a hormone, for example a polypeptide hormone such as a calcitonin, e.g. salmon calcitonin, a growth hormone, including human growth hormones (hGH), recombinant human growth hormones (rhGH), bovine growth hormones, and porcine growth hormones; growth hormone-releasing hormones and a pituitary thyroid hormone, for example.

The poly(amino acid) is preferably a pharmaceutically active ingredient.

Contrary to popular belief, it has surprisingly been found that faster disintegration of the pharmaceutical compositions of the present invention in a subject, e.g. the stomach, provides the best absorption characteristics for the active peptides and proteins, where major peptide or protein degradation occurs by pepsin or other enzymes.

A particularly preferred class of pharmaceutical compositions comprises salmon calcitonin as active ingredient. The poly(amino-acid) may be in free or salt form.

The poly(amino acid) such as, for example, calcitonin may be preferably present in an amount of between 0.03 wt % and 1 wt %, particularly between 0.05 wt % and 1 wt %, more particularly between 0.03 wt % and 0.5 wt % of the total mass of the pharmaceutical composition. In particular, the poly(amino acid) such as, for example, calcitonin may be present in an amount of between 0.05 and 0.5 wt %, e.g. 0.1 to 0.2 wt %. For example, where the final pharmaceutical composition weight is 500 mg, this equates to amounts of poly (amino acid), for example calcitonin, of from 0.25 mg to 5 mg.

The delivery agent may be any delivery agent suitable for delivering poly(amino acid)s by oral administration. The delivery agents useful in the formulation, e. g. the oral formulation, are any agents useful for delivering the particular pharmacologically active agent. Suitable delivery agents are any one of the modified amino acids disclosed in aforementioned U.S. Pat. No. 5,866,536 or any one of the modified amino acids described in the aforementioned U.S. Pat. No. 5,773,647 or any combination thereof. The contents of the aforementioned U.S. Pat. Nos. 5,773,647 and 5,866,536 are hereby incorporated by reference in their entirety.

In addition, the delivery agent can be the disodium salt of any of the aforementioned modified amino acids as well as ethanol solvates and hydrates thereof. Suitable compounds include compounds of the following formula I

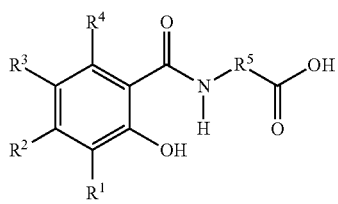

Formula I wherein
$R^1$, $R^2$, $R^3$, and $R^4$ are independently hydrogen, —OH, —$NR^6R^7$, halogen, $C_1$-$C_4$alkyl, or $C_1$-$C_4$alkoxy;
$R^5$ is a substituted or unsubstituted $C_2$-$C_{16}$alkylene, substituted or unsubstituted $C_2$-$C_{16}$alkenylene, substituted or unsubstituted $C_1$-$C_{12}$alkyl(arylene), or substituted or unsubstituted aryl($C_1$-$C_{12}$alkylene); and
$R^6$ and $R^7$ are independently hydrogen, oxygen, or $C_1$-$C_4$ alkyl; and hydrates and alcohol solvates thereof. The compounds of formula I as well as their disodium salts and alcohol solvates and hydrates thereof are described in WO 00/059863, along with methods for preparing them.

In addition, the delivery agent can be the disodium salt of any of the aforementioned modified amino acids as well as ethanol solvates and hydrates thereof.

The disodium salt may be prepared from the ethanol solvate by evaporating or drying the ethanol solvate by methods known in the art to form the anhydrous disodium salt. Drying is generally carried out at a temperature of from about 80 to about 120° C., preferably from about 85 to about 90° C., and most preferably at about 85° C. The drying step is generally performed at a pressure of 26"Hg or greater. The anhydrous disodium salt generally contains less than about 5% by weight of ethanol and preferably less than about 2% by weight of ethanol, based on 100% total weight of anhydrous disodium salt. The disodium salt of the delivery agent can also be prepared by making a slurry of the delivery agent in water and adding two molar equivalents of aqueous sodium hydroxide, sodium alkoxide or the like.

Suitable sodium alkoxide include, but are not limited to, sodium methoxide, sodium ethoxide, and combinations thereof. A still further method of preparing the disodium salt is by reacting the delivery agent with one molar equivalent of sodium hydroxide to yield the disodium salt. The disodium salt can be isolated as a solid by concentrating the solution containing the disodium salt to a thick paste by vacuum distillation. This paste may be dried in a vacuum oven to obtain the disodium salt of the delivery agent as a solid. The solid can also be isolated by spray drying an aqueous solution of the disodium salt. The delivery agents may be prepared by methods known in the art, e. g., as mentioned above, by methods described in U.S. Pat. Nos. 5,773,647 and 5,866,536. The ethanol solvates, as described in the aforementioned WO 00/059863, include, but are not limited to, a molecular or ionic complex of molecules or ions of ethanol solvent with molecules or ions of the disodium salt of the delivery agent. Typically, the ethanol solvate contains about one ethanol molecule or ion for every molecule of disodium salt of the delivery agent. The ethanol solvate of the disodium salt of the delivery agent can be prepared by dissolving the delivery agent in ethanol. Typically, each gram of delivery agent is dissolved in from about 1 to about 50 mL of ethanol and generally, from about 2 to about 10 mL of ethanol. The delivery agent/ethanol solution is then reacted with a molar excess of a sodium containing salt, such as a monosodium containing salt, relative to delivery agent, i. e. for every mole of delivery agent there is more than one mole of sodium cations, yielding the ethanol solvate. Suitable monosodium salts include, but are not limited to, sodium hydroxide; sodium alkoxide, such as sodium methoxide and sodium ethoxide; and any combination of the foregoing.

Preferably, at least about two molar equivalents of the monosodium containing salt are added to the ethanol solution, i. e. for every mole of delivery agent there is at least about two moles of sodium cations. Generally, the reaction is performed at or below the reflux temperature of the mixture, such as at ambient temperature. The ethanol solvate is then recovered by methods known is the art, such as, concentration of the resulting slurry at atmospheric distillation, cooling the concentrated slurry and filtering the solid. The recovered solid can then be vacuum dried to obtain the ethanol solvate. The hydrates of the disodium salts of the delivery agents may be prepared by drying the ethanol solvate to from an anhydrous disodium salt, as described above, and hydrating the anhydrous disodium salt. Preferably, the monohydrate of the disodium salt is formed. Since the anhydrous disodium salt is very hydroscopic, the hydrate forms upon exposure to atmospheric moisture.

Generally, the hydrating step is performed at from about ambient temperature to about 50° C., preferably ambient temperature to about 30° C. and in an environment having at least 50% relative humidity. Alternatively, the anhydrous disodium salt may be hydrated with steam.

The preferred delivery agents may be selected from N-(5-chlorosalicyloyl)-8-aminocaprylic acid (5-CNAC), N-(10-[2-hydroxybenzoyl]amino) decanoic acid (SNAD), N-(8-[2-hydroxybenzoyl]amino) caprylic acid (SNAC) and their mono- and di-salts, for example monosodium and disodium salts, ethanol solvates of their salts and the monohydrates of their salts and any combinations thereof, such as ethanol solvates of their sodium salts and the monohydrates of their sodium salts and any combinations thereof, for example. Other salts, such as potassium, lithium and calcium are also contemplated. The delivery agents 5-CNAC, SNAD, and SNAC are very water soluble, especially in the alkaline conditions of the intestine and nearly fully, i. e. greater than 90%, absorbed by the gastro-intestinal tract, such as the duodenum for example, whether ingested in micronized or coarse form. Conversely, the delivery agents may form precipitates in an acidic environment, for example in the stomach. Preferably, the delivery agent is in micronized form.

A particularly surprising aspect of the present invention is the effect the chosen delivery agent may have on the dissolution time of the active ingredient. For example, where the carrier is 5-CNAC, the transformation of an insoluble form, e.g. the solid form of sodium salt or free acid of 5-CNAC in a particular environment, for example the intestine environment, to a soluble form, e.g. the 5-CNAC in solution provides a mechanism whereby the active ingredient has a high dissolution rate, e.g. not more than ten minutes.

It is therefore hypothesized that any insoluble form of a delivery agent, which transforms into a soluble entity upon contact within the gastro intestinal environment (such as that of the duodenum environment, for example) may provide a mechanism for a high dissolution rate of an active ingredient.

Therefore, the delivery agent, such as 5-CNAC, for example or its salts, may provide a satisfactory, or optimum, microenvironment for the satisfactory, or optimum, rate of dissolution and/or absorption of a poly (amino acid) active ingredient.

In particular, the disodium salt of 5-CNAC may provide a satisfactory, or optimum, microenvironment for the absorption of salmon calcitonin. The absorption of the salmon calcitonin may be measured by plasma concentration, for example.

In a particularly preferred class of pharmaceutical compositions, the delivery agent is 5-CNAC. The 5-CNAC may be in free or salt form and may consist of a wide range of particle sizes ranging from, for example, 50 to 5 μm average particle size.

Preferably, the delivery agent is in micronized form.

The average particle size of the micronized delivery agent, e.g. 5-CNAC, may be measured by milling coarse 5-CNAC and sampling periodically with reference particle size measurements to identify when the averaged desired particle size is achieved. A process for micronising 5-CNAC is described in WO 2005/014031, which is incorporated herein by reference; see in particular page 10 and example 1, which describe the effects of different 5-CNAC size particles.

The delivery agent is preferably present in an amount of between 5 wt % and 80 wt %, particularly of between 10 wt % and 70 wt %, more particularly of between 20 wt % and 60 wt %, even more particularly of between 40 wt % and 60 wt % of the total mass of the pharmaceutical composition, for example 50 wt %. Where the final pharmaceutical composition weight is 500 mg, this equates to amounts of 2.5 to 400 mg of the delivery agent present in the final pharmaceutical composition.

In addition, where the delivery agent is 5-CNAC or salt thereof, its salt form is preferably present in amount of more than 90% weight per total weight of the 5-CNAC present in the composition, this particularly applies when the disodium salt of 5-CNAC is present.

The preferred delivery agent is the disodium salt of 5-CNAC.

The active ingredient to delivery agent ratio is preferably present between 1/25 to 1/400, particularly between 1/50 to 1/300, more particularly between 1/100 to 1/200, with the most preferred ratio in the case sCT/5-CNAC compositions being of 0.5 mg-1 mg sCT to 200 mg-300 mg of 5-CNAC disodium salt.

The disintegrant may be selected from any superdisintegrant, for example, synthetic polymers capable of swelling through absorption of water, of which crospovidones and povidones may be mentioned in particular. More specific examples of disintegrants are crospovidone, povidone. Explotab or AC-Di-Sol. In a preferred class of pharmaceutical compositions, the disintegrant is Crospovidone. Crospovidone is a synthetic crosslinked homopolymer of N-vinyl-2-pyrrolidone, also called 1-ethenyl-2-pyrrolidinone, having a molecular weight of 1,000, 000 or more.

Superdisintegrants are agents that can absorb water and swell to a significant extent by either wicking effect or hydration. They are more efficient than conventional disintegrant due to their water uptake and swelling capacity.

Other agents may also be used that decrease disintegration time by effervescent and/or other means.

The disintegrant is preferably present in an amount from 0.02 wt % to 10 wt %, particularly from 0.2 wt % to 10 wt %, more particularly from 1.0 wt % to 8 wt %, e.g. 3 wt % to 7% of the total mass of the pharmaceutical composition, for example 5 wt %. Where the final pharmaceutical composition weight is 500 mg, this equates to amounts of the disintegrant between 0.1 mg to 50 mg.

Commercially available crospovidones include Polyplasdone XL, Polyplasdone XL-10, PolyplasdonelNF-10 available from ISP, Kollidon CL, available from BASF Corporation. The preferred crospovidone is Polyplasdone XL. Povidone is a synthetic polymer consisting of linear 1-vinyl-2-pyrrolidinone groups having a molecular weight generally between 2,500 and 3,000, 000. Commercially available povidones include Kollidon K-30, Kollidon K-90F available from BASF Corporation and Plasdone K-30 and PlasdoneK-29132, available from ISP. Alternatively, they may be synthesized by known processes.

The diluent may be, for example Avicel PH 102 or 101. The diluent may be present in the pharmaceutical composition of up to 90 wt % based on the whole composition, or may be used to make up any difference between the desired and actual final pharmaceutical composition mass, which may be, for example up to 600 mg, e.g. 500 mg. Preferably, the binder is present in an amount of between 20 and 70 wt % based on the whole composition, e.g. 40 to 60 wt %, e.g. 50 wt %. Where the final pharmaceutical composition weight is 500 mg, this equates to amounts of, for example, 100 mg to 350 mg.

In a preferred embodiment of the present invention, the diluent is a microcrystalline cellulose.

The addition of a diluent will decrease the disintegration times of a tablet.

The dissolution times of an active agent may be independent of the diluent.

The addition of a glidant or lubricant to a tablet may increase dissolution rate of an active ingredient, this is known to the person in the field due to the hydrophobicity of the lubricant, i.e. magnesium stearate, sodium stearyl fumarate, calcium stearate etc.

Disintegration and Dissolution

The terms disintegration and dissolution may be defined under USP sections <701> and <711>, which is incorporated herein by reference.

By "dissolution time" according to the present invention the time is to be understood, which is required for a given amount (or fraction) of a drug to be released into solution from a solid dosage form. Dissolution time is measured in vitro, under conditions that simulate those that occur in vivo, in experiments in which the amount of drug in solution is determined as a function of time.

For example, dissolution may be determined by the USP XXIII Paddle Method using a USP dissolution test apparatus 2 at 50 rpm.

By "disintegration time ("DT")" according to the present invention the time is to be understood which is required for the formulated drug product (i.e. a capsule or tablet) to break into primary particles under carefully specified test conditions. The conditions of the laboratory test, in vitro, are set to simulate those that occur in vivo.

For example, where the composition is in a tablet form, the disintegration time is the time which is required for a tablet to break up into granules of specified size. Factors such as the kind and amount of tablet binders and the degree of compression used in compacting the tablet ingredients are determinative of the disintegration time.

The disintegration time of the pharmaceutical composition according to the present invention is no more than 10 minutes, e.g. it may be not more than 9 minutes. Preferably, the disintegration time is up to 8 minutes, e.g. 6 minutes, for example it may be less than 8 minutes, as in the case of 7 minutes. In a further class of pharmaceutical compositions the DT is up to 5 minutes, e.g. between 1 and 4 minutes such as 2 minutes, for example. In still a further class of pharmaceutical compositions, the disintegration times are less than two minutes. e.g. 1 minute or less.

It is therefore a further aspect of the present invention that the compositions have a dissolution time of up to ten minutes.

In summary, the disintegration times of the compositions of the present invention are any of 1, 2, 3, 4, 5, 6, 7, 8, 9 or 10 minutes or any fraction thereof, such as for example 10, 20, 30, 40, 50, 60, 70, 80, 90, 100, 120, 130, 140, 150, 160, 170, 180 seconds etc.

Disintegration refers here to the physical process by which a tablet breaks down into fine particles, for example of less than 0.065 cm in diameter. This process is monitored visually and pertains to the physical integrity of the tablet alone. In a typical way, disintegration is performed by monitoring the time it takes for 100% of dispersed particles to pass through a coarse meshed cylinder, for example 7.75 cm log with an inside diameter of 21.5 mm and a wall approximately 2 mm thick in a water bath which is maintained at 37° C. (±2° C.), as per USP <701>.

The disintegration time of a composition may be linked with the dissolution time. The dissolution time is the time in which an active ingredient is dissolved into a liquid medium. Dissolution is monitored via UV or HPLC analysis and provides the approximate time required for full release of a drug.

The active ingredients in a disintegrated composition such as, for example, a tablet are not necessarily found to be in solution and available for absorption. A long disintegration time is incompatible with rapid drug absorption; a short disintegration time, by itself, does not ensure rapid absorption.

Typically, there is some relationship between disintegration and dissolution. For the compositions of the present invention a linear relationship could be established between the dissolution time and the disintegration time. In the current example it could be demonstrated that shorter disintegration time corresponds to faster dissolution whereas longer disintegration time relates to slower dissolution. More specifically, a disintegration time of 6 min and below corresponds to dissolution of >90% at 20 minutes, a disintegration time of 9 mins corresponds to dissolution of ~30% at 20 minutes.

In a specific embodiment of the invention, the dissolution time of the compositions has a linear relationship with the dispersion time of the compositions. As such, in yet another aspect of the present invention, the disintegration time of the composition may be used to predict the dissolution time of the composition. Equally, where the dissolution time of the composition is known, the disintegration time of the composition may be calculated.

The use of the relationship between the disintegration time and the dissolution time is particularly effective where the composition is in tablet form. Here, the disintegration time will be the disintegration time of the tablet in the stomach. Therefore, factors having an effect on the disintegration time of the tablet, e.g. tablet hardness, may also be used to predict the dissolution time of an active ingredient.

The extent of dissolution may be reflected in the degree of absorption. Therefore, a successful dissolution parameter is one in which a therapeutically effective amount of the active substance, or substances, reaches the blood plasma.

In a monkey pharmacokinetic study, a formulation containing 0.8 mg of calcitonin should provide a peak plasma concentration ($C_{max}$) of no less than 400 pg/mL and/or reduction in plasma calcium level of >20% in 6 hrs.

Therefore, it is contemplated that by adjusting the disintegration time of the compositions of the invention, the rate and/or amount of absorption may be optimized and/or changed as required. As an example, where the composition is in tablet form, the bioavailability may be adjusted by adjusting the tablet hardness, for example. As such, the ingredients (excipients/carriers) of a tablet and the degree of compression in forming the tablet may influence the bioavailability of an active ingredient in a composition of the present invention.

In yet another class of compounds according to the present invention, the pharmaceutical composition is in the form of a compressed tablet. In this form, the tablet preferably has a hardness of between 5 and 10 kilopascal.

In this class of compounds, the tablet hardness may be used to additionally determine the disintegration time of the pharmaceutical composition. It has been found by the present inventors that, using the same pharmaceutical composition, the tablet hardness has a linear relationship with disintegration time. Therefore, it is another aspect of the present invention that the disintegration time of the pharmaceutical composition, depends on the hardness of the tablet. More specifically, certain disintegration time can be achieved by controlling the hardness of the tablets compressed.

Tablet Hardness

A tablet at preferred mass with preferred formulation that has a hardness between 5-20 Kp would typically has disintegration time of less than 6 mins.

Figure 3:
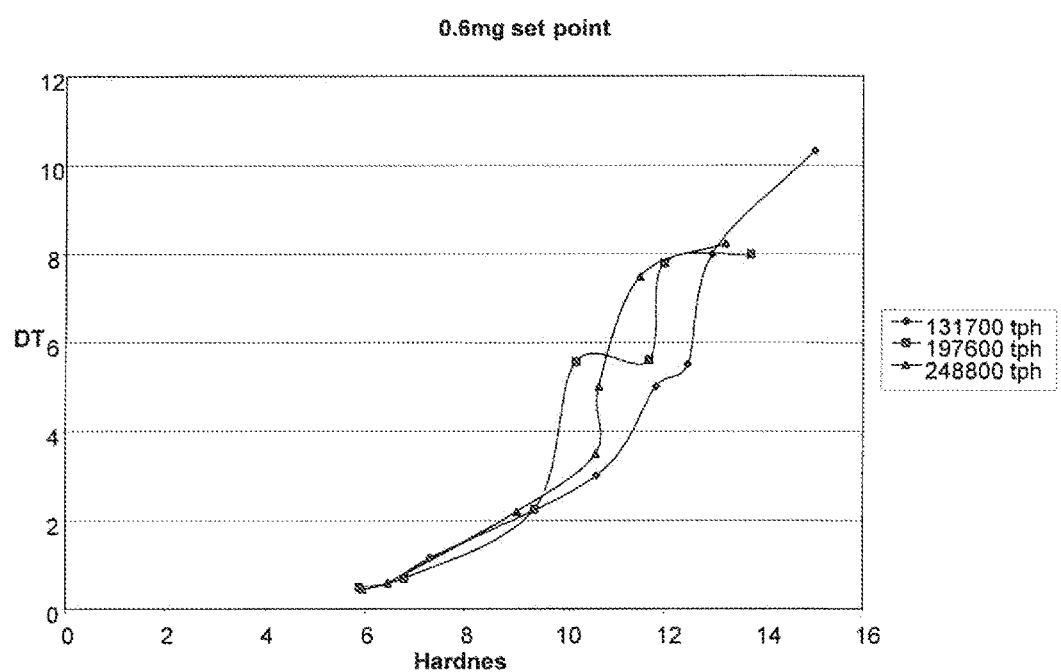
FIG. 3 is a graph illustrating the effect of tablet hardness on disintegration time.
Figure 4:
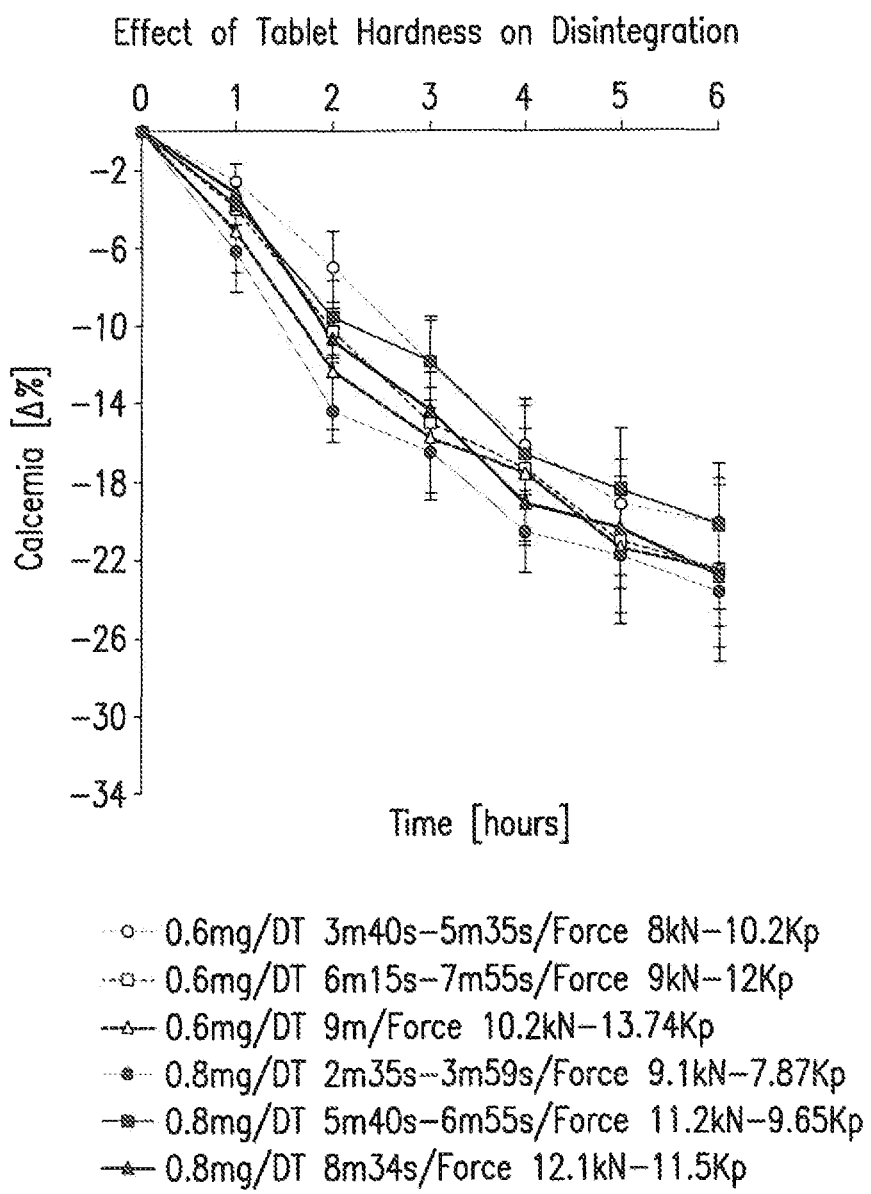
FIG. 4 is a graph illustrating the effect of tablet hardness on disintegration time.

The hardness of a tablet is directly related to the disintegration time of the tablet, as shown by Tables I and 2 below and FIGS. 3 and 4.

TABLE 1

0.6 mg
Speed: 197600 tab/hr
which is 27 rpm

| Force (KN) | Weight (mg) | Weight RSD | Thickness (mm) | Hardness (Kp) | Hardness range | DT | Friability |
|---|---|---|---|---|---|---|---|
| 5.5 | 500.58 | 0.58 | 4.95 | 5.88 | 5.7-6.1 | 30 s | |
| 6 | 504.15 | 0.89 | 4.86 | 6.79 | 5.7-7.7 | 40 s | 0.73 |
| 7.1 | 503.68 | 1.01 | 4.6 | 9.41 | 8.3-10.4 | 2 m 30 s-2 m 15 s | 0.25 |

TABLE 1-continued 0.6 mg
Speed: 197600 tab/hr
which is 27 rpm

| Force (KN) | Weight (mg) | Weight RSD | Thickness (mm) | Hardness (Kp) | Hardness range | DT | Friability |
|---|---|---|---|---|---|---|---|
| 8 | 499.68 | 0.69 | 4.52 | 10.24 | 9.8-10.9 | 3 m 40 s-5 m 35 s | 0.52 |
| 8.5 | 502.04 | 0.93 | 4.47 | 11.7 | 11.2-12.8 | 4 m 30 s-5 m 46 s | 0.25 |
| 9 | 505.74 | 0.62 | 4.43 | 12 | 11.7-12.6 | 6 m 15 s-7 m 55 s | 0.14 |
| 10.2 | 504.8 | 0.57 | 4.31 | 13.74 | 12.8-14.6 | 7 m 19 s-8 m 8 s | |

TABLE 2

0.8 mg
Speed: 329400 tab/hr
which is 45 rpm

| Force (KN) | Weight (mg) | Weight RSD | Thickness (mm) | Hardness (Kp) | Hardness range | DT | Friability |
|---|---|---|---|---|---|---|---|
| 5.1 | 497.01 | 0.67 | 4.88 | 2.94 | 2.4-3.1 | 20 s | 1.1 (severe chipping) |
| 6.4 | 497.97 | 0.75 | 4.66 | 4.22 | 3.7-4.7 | 30-35 s | 0.38 (slight chipping) |
| 7 | 499.49 | 1 | 4.5 | 5.26 | 4.6-6.0 | 1 m 10 s | 0.44 |
| 8 | 496.66 | 0.57 | 4.43 | 6.51 | 6.0-7.1 | 2 m 42 s | 0.14 |
| 9.1 | 497.56 | 0.55 | 4.31 | 7.87 | 7.5-8.3 | 2 m 35 s-3 m 59 s | 0.1 |
| 10 | 503.16 | 0.71 | 4.25 | 8.34 | 8-8.9 | 3 m 40 s-4 m 30 s | 0.05 |
| 11.2 | 503.21 | 0.66 | 4.18 | 9.65 | 9.3-10.1 | 5 m 40 s-6 m 55 s | 0.03 |

Where:
RSD is Relative Standard Deviation; and
DT is disintegration time

Thus the compression force applied to a particular composition when manufacturing a tablet may determine the disintegration time of the pharmaceutical composition.

Additional Ingredients

In further classes of compositions, the pharmaceutical composition additionally comprises a glidant agent and/or a stabiliser and/or a dry binder.

Thus in one class of pharmaceutical compositions, the pharmaceutical composition additionally comprises a glidant agent.

The glidant agent is, for example cab-o-sil.

The glidant agent may be present in an amount up to 1.5 wt %. e.g. 0.02 to 0.5 wt % based on the whole composition, e.g. 0.3 wt %. Where the final pharmaceutical composition weight is 500 mg, this equates to amounts of up to 7.5 mg.

In a further class of pharmaceutical compositions, the pharmaceutical composition additionally comprises a lubricant. The lubricant is for example magnesium stearate.

The lubricant may be present in an amount of, for example 0.5 to 1.5 wt % based on the whole composition, e.g. 0.75 to 1.25 wt %, e.g. 1 wt %. Where the final pharmaceutical composition weight is 500 mg, this equates to amounts of 2.5 mg to 7.5 mg.

In addition to the specific ingredients mentioned herein, the compositions of the present invention, having the disintegration and/or dissolution properties as mentioned herein may also be combined with other technologies such as those described in WO 94/26778; U.S. Pat. No. 5,359,030; U.S. Pat. No. 5,438,040; U.S. Pat. No. 5,681,811; U.S. Pat. No. 6,191,105; U.S. Pat. No. 6,309,633; U.S. Pat. No. 6,380,405; U.S. Pat. No. 6,436,990; U.S. Pat. No. 6,458,776; WO 97/33531; U.S. Pat. No. 5,912,014; U.S. Pat. No. 608,618 and U.S. Pat. No. 6,479,692 (the content thereof is hereby incorporated by reference in its entirety).

Methods

The present invention includes methods for making the formulations and compositions described herein.

In particular, the present invention relates to a method for making a tablet having a disintegration time of not more than 10 minutes, the method comprising:
 a. Mixing a poly(amino acid), delivery agent and disintegrant together to form a mixture
 b. Adding to the mixture a diluent and mixing.
 c. Compressing the product.

Optionally, the method can additionally comprise and of the following:
1. Sieving the mixture of part a.
2. Adding a disintegrant and mixing after step b
3. Adding a lubricant and/or glidant prior to step c.

Figure 6:
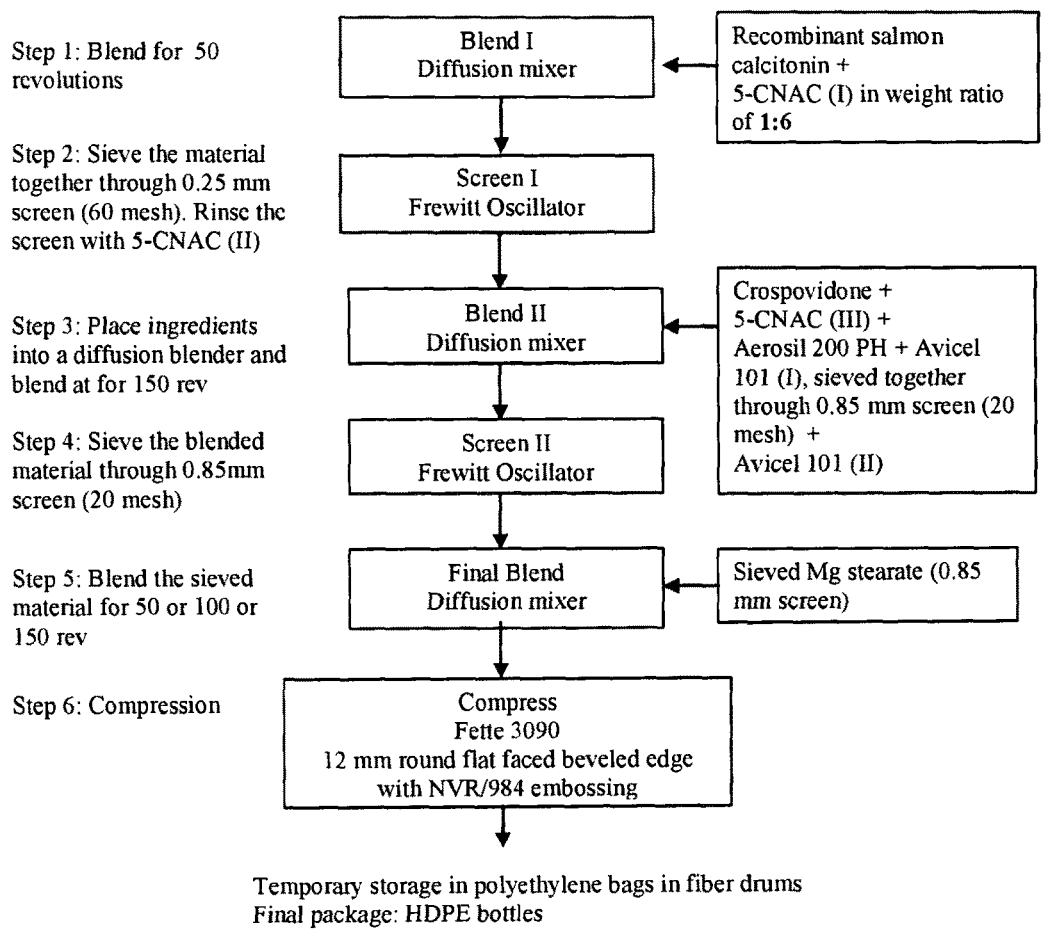
FIG. 6 shows a scheme for an exemplary method of making a tablet having a disintegration time of not more than 10 minutes.

An exemplary method is shown in FIG. 6.

In one embodiment of the above method, the compressing of the mixture into a tablet provides a tablet having a hardness of between 5 and 20 pa and such that the tablet has a disintegration time of not more than 10 minutes.

As mentioned above, when the poly(amino acid) is calcitonin, the formulation of the present invention may be used to treat a bone resorption disorder, such as osteoporosis, osteolyisis or Paget's disease, for example, or an arthritic condition, such as osteoarthritis, for example. To this end, there is provided a method of preventing or/and treating a bone resorption disorder and/or an arthritic condition in a patient in need thereof comprising administering to said patient a therapeutically effective amount of the pharmaceutical composition according to the present invention, where the poly(amino acid) is calcitonin, e.g. salmon calcitonin in free form or salt form and the disintegration time of the pharmaceutical composition is up to 10 mins.

In addition, the pharmaceutical composition of the present invention may be used, when containing the required poly (amino acid), e.g. calcitonin, in the following:

1. A method of inhibiting resorption and normalizing turnover of sub-chondral bone in a patient in need thereof comprising administering to said patient a therapeutically effective amount of the pharmaceutical composition according to the present invention.
2. A method of preserving and stimulating cartilage via a direct or indirect effect on chondrocytes in a patient in need thereof comprising administering to said patient a therapeutically effective amount of the pharmaceutical composition according to the present invention.
3. A method of inhibiting phospholipase A2 and/or collagenase activity in a patient in need thereof comprising administering to said patient a therapeutically effective amount of the pharmaceutical composition according to the present invention.
4. A method of obtaining stimulatory effect onglycosaminoglycan and/or proteoglycan synthesis in a patient in need thereof comprising administering to said patient a therapeutically effective amount of the pharmaceutical composition according to the present invention.
5. A method of acting on the inhomogeneity in density or stiffness of the subchondral bone in a patient in need thereof comprising administering to said patient a therapeutically effective amount of the pharmaceutical composition according to the present invention.
6. A method of acting on the inflammatory process, leading to attenuations on pain in motion and related symptoms (e.g. circumference of knee, flexion angle of the knee, swelling stiffness) in a patient in need thereof comprising administering to said patient a therapeutically effective amount of the pharmaceutical composition according to the present invention.
7. A method to reduce the degenerative change in the joint in a patient in need thereof comprising administering to said patient a therapeutically effective amount of the pharmaceutical composition according to the present invention.

Combinations

In another aspect of the Invention, the pharmaceutical composition according to the present invention may be administered with, e.g. Include, a second drug substance, where the said second drug substance is, for example a second bone resorption inhibitor, bone forming drug or pain reducing drug.

Where the pharmaceutical composition according to the invention is administered with a second, third or fourth drug substance, each substance may be independently administered simultaneously, separately or sequentially in relation to the composition of the present invention.

Suitable second drug substances may include a calcitonin of different origin, e.g. salmon, (Asu1-7)-eel or human calcitonin, a calcitonin analogue or derivative thereof, a steroid hormone, e.g. an estrogen, a partial estrogen agonist or estrogen-gestagen combination, a SERM (Selective Estrogen Receptor Modulator) e.g. raoxifene, lasofoxifene, TSE-424, FC1271, Tibolone (Livial O), vitamin D or an analogue thereof or PTH, a PTH fragment or a PTH derivative e.g. PTH (1-84), PTH (1-34), PTH (1-36), PTH (1-38), PTH (1-31) NH2 or PTS 893, bisphosphonates (e.g. alendronate, risedronate, zoledronic acid, ibandronate); protease inhibitors, e.g. Cathepsin inhibitor, preferably a cathepsin K inhibitor; PTH releases; SARMs (selective androgen receptor molecules); MMP inhibitors (metalloprotease inhibitors), strontium relate, COX-2 inhibitors, e.g. lumiracoxib (Prexige (E)), celecoxib (Celebrex0), rofecoxib (Vioxx (D), valdecoxib (BextraS)), etoricoxib (ArcoxiaG)), or mixed COX-1 and COX-2 inhibitors, e.g. diclofenac.

Thus, according to this aspect of the invention, there is provided a pharmaceutical combination comprising:
 a) a first agent which comprises a pharmaceutical composition comprising calcitonin, e.g. salmon, (Asu1-7)-eel or human calcitonin in free form or salt form, preferably in pharmaceutically acceptable oral delivery form, a delivery agent and a disintegrant, said pharmaceutical composition having a disintegration time of up to 10 minutes; and
 b) a co-agent which is bone resorption inhibitor, bone forming drug or pain reducing agent, e.g. as disclosed above.

The term "pharmaceutical combination" as used herein means a product that results from the mixing or combining of more than one active ingredient and includes both fixed and non-fixed combinations of the active ingredients. The term "fixed combination" means that the active ingredients, e.g. salmon calcitonin and a co-agent, are both administered to a patient simultaneously in the form of a single entity or dosage. The term "non-fixed combination" means that the active ingredients, e.g. salmon calcitonin and a co-agent, are both administered to a patient as separate entities either simultaneously, concurrently or sequentially with no specific time limits, wherein such administration provides therapeutically effective levels of the 2 compounds in the body of the patient.

Preferably the calcitonin, e.g. salmon calcitonin in free form or in pharmaceutically acceptable salt form, is co-administered with a protease inhibitor, e.g. cathepsin inhibitor, e.g. cathepsin K inhibitor.

As part of the above aspect of the invention, there is also provided a kit of parts for use in the prevention and/or treatment of a bone resorption disorder and/or an arthritic condition, said kit comprising:
a) a first agent which is a calcitonin, e.g. salmon, (Asu1-7)-eel or human calcitonin in free form or salt form, in pharmaceutical composition having
(i) a poly(amino acid)
(ii) a delivery agent
(iii) a disintegrant; and
a disintegration time of up to 10 minutes; and
b) a co-agent which is a bone resorption inhibitor, bone forming drug or pain reducing agent, e.g. as disclosed above.

In addition, there are also provided co-administration methods for each of the methods (i) to (vii) above, where the methods comprise the co-administration of a therapeutically effective amount of the pharmaceutical composition according to the present invention, e.g. a pharmaceutical composition containing calcitonin, e.g. salmon calcitonin in free form or salt form, in a pharmaceutical composition having a disintegration time of up to 10 minutes, and a second drug substance, said second drug substance being a bone resorption inhibitor, bone forming drug or pain reducing drug in free form or salt form.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

Dosages

When the pharmacologically active agent is salmon calcitonin, the appropriate dosage will, of course, vary depending upon, for example, the host and the nature and severity of the condition being treated. However, in general, satisfactory results will be obtained systemically at daily dosages of from about 0.5 µg/kg to about 10 µg/kg animal body weight, preferably 1 µg/kg to about 6 µg/kg body weight. The pharmaceutical acceptable inactive excipients which are used in the pharmaceutical composition of calcitonin, e.g. in the oral pharmaceutical composition of calcitonin, may include polymers and inactive compounds which for example, aid the pharmaceutical composition or manufacturing of the solid oral dosage form contemplated by the present invention or which may aid the release of the solid oral composition in the gastro-intestinal environment.

The disclosure provides provision of a particular dosage range for a calcitonin, particularly a calcitonin in free or salt form, e.g. salmon calcitonin, which is efficacious and well tolerated, i. e. safe for a patient to take.

Preferred is a range from 0.15 mg to 2.5 mg, particularly from 0.4 mg to 2.5 mg of salmon calcitonin for a patient, e.g. human, e.g. an average human of about 70 kg. More preferred are doses around 1 mg, e.g. from 0.8 mg to 1.2 mg. Also preferred are doses not more than 1 mg but at least 0.4 mg. More preferred is a dose of about 1 mg, e.g. 1 mg. Most preferred is a dose of between 0.5 mg and 1.1 mg, in particular, from 0.6 mg to 0.8 mg, more particularly a dose of from 0.15 mg to 0.4 mg, but especially a dose of 0.15 mg. The does may be administered once per day to a patient in need thereof.

To this end, the pharmaceutical compositions of the present invention may be used for the following:

A method of preventing or/and treating osteoarthritis in a patient in need thereof comprising administering to said patient a pharmaceutical composition comprising between 0.4 and 2.5 mg, preferably between 0.8 and 1.2 mg, most preferred about 1 mg, of a calcitonin, e.g. salmon calcitonin and having a disintegration time of up to 10 minutes.

A pharmaceutical composition comprising between 0.4 and 2.5 mg, preferably between 0.8 and 1.2 mg, most preferred about 1 mg of a calcitonin, e.g. salmon calcitonin.

The use of a calcitonin, e.g. salmon calcitonin, in the manufacture of a medicament for the treatment and/or prevention of a bone resorption disorder and/or an arthritic condition, wherein said medicament comprises calcitonin in an amount from 0.4 to 2.5 mg, preferably between 0.8 and 1.2 mg, most preferred about 1 mg, of a calcitonin, e.g. salmon calcitonin where said pharmaceutical composition has a disintegration time of up to 10 minutes.

Such oral delivery form is e.g. a pharmaceutical composition for oral delivery of salmon calcitonin comprising:
(A) a therapeutically effective amount of said salmon calcitonin;
(B) at least one absorption enhancer effective to promote bioavailability of said salmon calcitonin
said composition having a disintegration time of up to 10 mins.

Examples of enhances include 5-CNAC, SNAC and fatty acids such as Na Caprate, Na Capralate.

The pharmaceutical compositions with which the usefulness of calcitonin in the treatment of osteoarthritis is shown, may be provided as a capsule including a soft-gel capsule, tablet, caplet, suppository or other solid oral dosage form, all of which can be prepared by methods well known in the art, provided that the composition has a disintegration time of up to 10 minutes.

In particularly preferred formulation of the present invention, the compositions have a disintegration time of up to 10 minutes. Or if tested in appropriate condition, it has more than 90% of content dissolved in 20 minutes.

In a general overview of the process of the present invention, the solid pharmaceutical compositions may be prepared by first grinding either the delivery agent or the delivery agent with any combination of the additional ingredients of the present composition to a micronized particle size. The micronized delivery agent or micronized delivery agent plus micronized additional ingredients of the present invention may then be further processed by conventional methods e.g. by blending a mixture of the active agent or active agents, the delivery agent, the crospovidone or povidone and/or other ingredients, kneading, and filling into capsules or, instead of filling into capsules, molding followed by further tableting or compression-molding to give tablets. In addition, a solid dispersion may be formed by known methods followed by further processing to form a tablet or capsule.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

EXAMPLES

The following examples serve to further illustrate the invention and will be readily understood by one of ordinary skill in the art. The examples are not meant to be limiting of the present invention in any way.

Example 1

Pharmaceutical Composition 1

| Ingredient | Amount (mg) | Percent |
|---|---|---|
| Salmon calcitonin | 0.8 | 0.16 |
| Micronized 5-CNAC | 228 | 45.6 |
| Avicel PH 102(E) | 241 | 47.94 |
| Crospovidone, NF | 25 | 5 |
| Magnesium stearate | 5 | 0.3 |
| Total | 500 | |

Figure 5A:
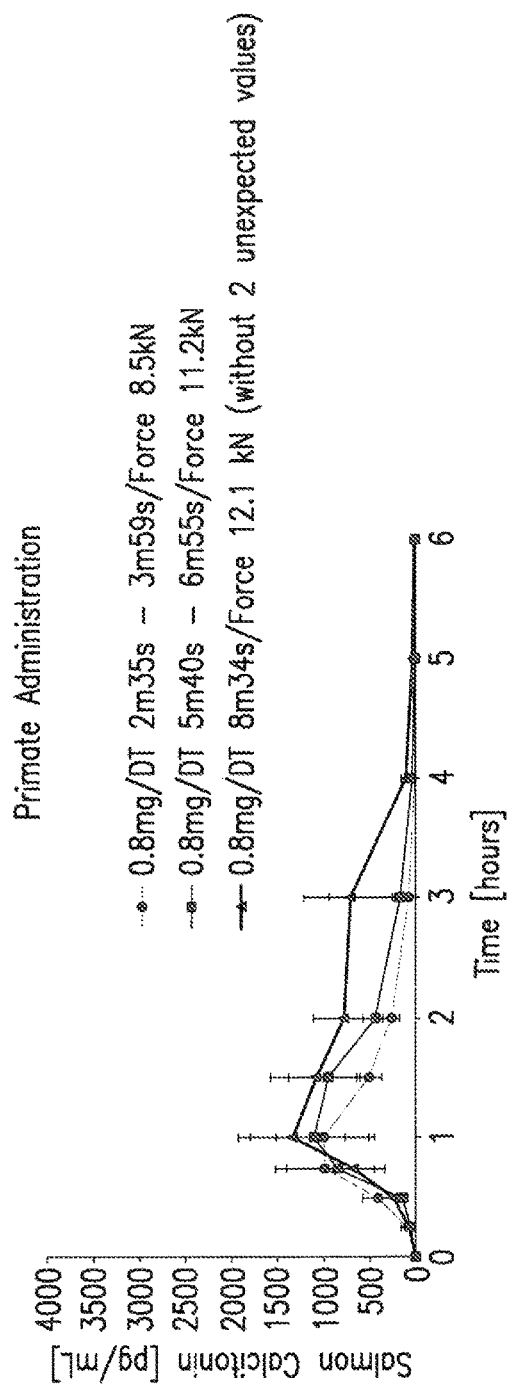
FIGS. 5a and 5b are graphs illustrating the effects of the administration of salmon calcitonin in primates.
Figure 5B:
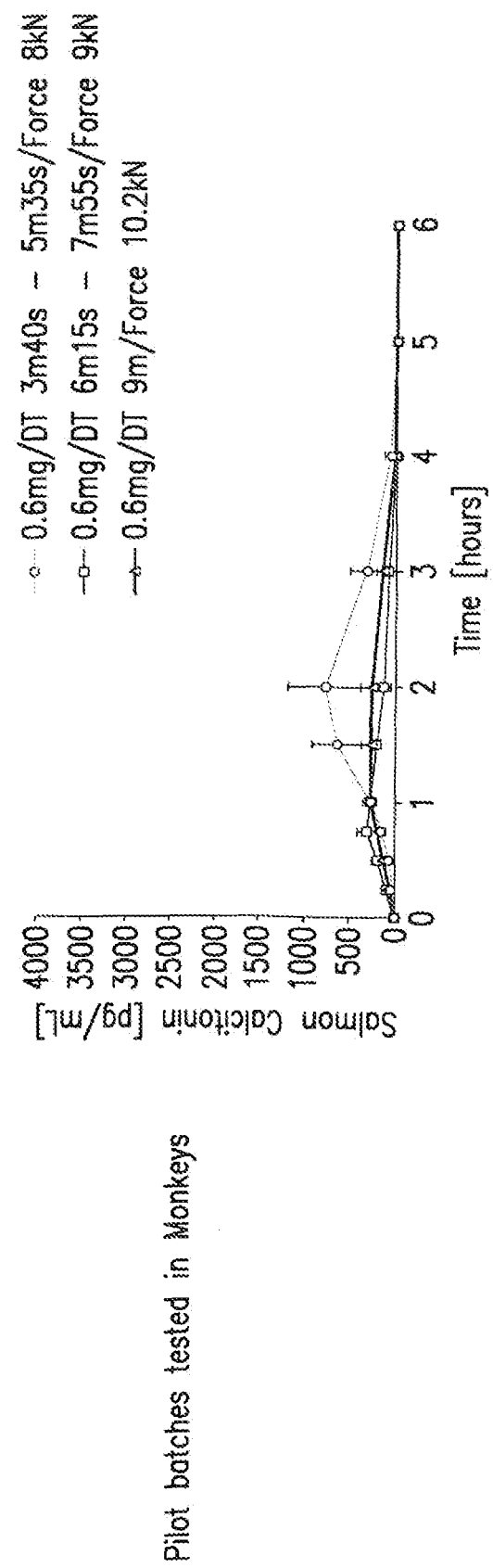

Salmon calcitonin, 5-CNAC and crospovidone were blended together in a first blending step. Avicel PH 102 was screened and added to the mixture and blended in a second blending step. Magnesium stearate was then added and the mixture was blended further in a final blending step. The final blend was compressed into a 500 mg tablet and evaluated in a Rhesus monkey. The results are shown in FIG. 5.

Example 2

Alternative Pharmaceutical Composition (3 Batches)

The same composition as in Example 1 was made, i.e. a composition comprising:

| Ingredient | Amount (mg) | Percent |
| --- | --- | --- |
| Salmon calcitonin | 0.8 | 0.16 |
| Micronized 5-CNAC | 228 | 45.6 |
| Avicel PH 102(E) | 241 | 47.94 |
| Crospovidone, NF | 25 | 5 |
| Magnesium stearate | 5 | 0.3 |

However, in contrast to Example 1 Salmon calcitonin and Avicel PH 102 were blended in a first blending step. 5-CNAC and crospovidone were then added to the first blend in a second blending step. Finally, Magnesium Stearate was added in a final blending step.

The final blend was then compressed at 3 different compression levels to obtain 3 different batches of tablets each having a different hardness, in order to provide 3 different disintegration times:
(i) 1 min 10 secs DT
(ii) 5 mins 40 secs DT
(iii) 8 mins 51 secs DT

Example 3

Alternative Pharmaceutical Composition

A similar blend was made to that of Example 1, except that an amount of Cab-o-sil was added to form a composition comprising:

| Ingredient | Amount (mg) | Percent |
| --- | --- | --- |
| Salmon calcitonin | 0.6 | 0.12 |
| Micronized 5-CNAC | 228 | 45.6 |
| Avicel PH 102(E) | 241 | 47.94 |
| Crospovidone, NF | 25 | 5 |
| Cab-o-sil | 1.5 | 0.3 |
| Magnesium stearate | 5 | 1 |
| Total | 500 | |

Salmon calcitonin, 5-CNAC and crospovidone were blended in a first blending step. Avicel and Cab-o-sil were screened and added in a second blending step. Finally, Magnesium stearate was added in a final blending step. The final blend was compressed into a 500 mg tablet. The incorporation of Cab-o-sil improved the compression profile of the tablet.

Example 4

Alternative Pharmaceutical Composition

A composition was made as described in Example 3, except that the composition comprised:

| Ingredient | Amount (mg) | Percent |
| --- | --- | --- |
| Salmon calcitonin | 0.8 | 0.16 |
| Micronized 5-CNAC | 228 | 45.6 |
| Avicel PH 102(E) | 241 | 47.94 |
| Crospovidone, NF | 25 | 5 |
| Cab-o-sil | 1.5 | 0.3 |
| Magnesium stearate | 5 | 1 |
| Total | 500 | |

Example 5

Alternative Pharmaceutical Composition

| Ingredient | Amount (mg) | Percent |
| --- | --- | --- |
| Recombinant Salmon calcitonin | 0.6 | 0.12 |
| 5-CNAC (I) | 1.2 | 0.24a |
| 5-CNAC (II) | 226.8 | 45.36b |
| Avicel PH 101 (I) | 15a | 3a |
| Avicel PH 101 (II) | 224.9b | 44.9b |
| Crospovidone | 25 | 5 |
| Aerosil 200 PH | 1.5 | 0.3 |
| Magnesium stearate | 5 | 1.0 |
| Total tablet weight (mg) | 500 | 100 |

Unit weight (a+b) listed as 5-CNAC disodium salt, corresponding to combined weight of 200 mg 5-CNAC free acid.

Unit weight (a+b) of Avicel PH 101 (I) and (II) corresponds to combined weight of Avicel PH 101.

Example 6

Alternative Pharmaceutical Composition

| Ingredient | Amount (mg) | Percent |
| --- | --- | --- |
| Recombinant Salmon calcitonin | 0.8 | 0.16 |
| 5-CNAC (I) | 4.8a | 2.1a |
| 5-CNAC (II) | 4.8b | 2.1b |
| 5-CNAC (III) | 218.4c | 41.4c |
| Avicel PH 101 (I) | 15a | 3a |
| Avicel PH 101 (II) | 224.7b | 44.9b |
| Crospovidone | 25 | 5 |
| Aerosil 200 PH | 1.5 | 0.3 |
| Magnesium stearate | 5 | 1.0 |
| Total tablet weight (mg) | 500 | 100 |

Unit weight (a+b+c) listed as 5-CNAC disodium salt, corresponding to combined weight of 200 mg 5-CNAC free acid.

Unit weight (a+b) of Avicel PH 101 (I) and (II) corresponds to combined weight of Avicel PH 101.

The process for preparation of the above formulations are similar to that of the one described in Example 1. However, an alternative Example process for the formation of the compositions of the Examples, in particular of Examples 5 and 6 is described below:
1. Weigh 0.25 g of sCT DS;
2. Blend with Part I of 5-CNAC;
3. Sieve blended material from Step 2 through #60 (0.25 mm) screen;

4. Rinse the screen from Step 3 with Part II of 5-CNAC;
5. Sieve Aerosil 200 PH and Part I of Avicel PH101 through #20 (0.85 mm) mesh screen;
6. Add Avicel PH101 (Part II), sieved material from Step 5, 5-CNAC (Part III), sieved material from Step 4, Crospovidone into diffusion blender and blend for 150 revolutions;
7. Sieve the blended material through #20 mesh (0.85 mm) screen;
8. Sieve Mg Stearate through #20 mesh (0.85 mm) screen and add to blend from Step 7;
9. Lubrication for 50 revolutions
10. Compress the blend into 12 mm round FFBE tablets and emboss.

All the equipment used are the same as described in Example 1.

Example 7

Primate Administration

The following tablets were prepared by the methods as hereinbefore described and tested on Rhesus monkeys.

Batch A

| 1. | 0.8 mg, | DT 2 m 35 s, | Force 8.5 kN |
| 2. | 0.8 mg, | DT 5 m 40 s, | Force 11.2 kN |
| 3. | 0.8 mg, | DT 8 m 34 s, | Force 12.1 kN |

Batch B

| 1. | 0.6 mg, | DT 3 m 40 s-5 m 35 s, | Force 8 kN |
| 2. | 0.6 mg, | DT 6 m 15 s-7 m 55 s, | Force 9 kN |
| 3. | 0.6 mg, | DT 9 m, | Force 10.2 kN |

Batch C

| 1. | 0.8 mg, | DT 2 m | Force 8.3 kN |

The Rhesus monkeys fast overnight prior to dosing and are restrained in chairs fully conscious, for the duration of the study period. One tablet each Batch is administered to each monkey via a gavage tube followed by 10 mL of water. Rhesus monkey blood samples are collected immediately before administration and at 0.25, 0.5, 0.75, 1, 1.5, 2, 3, 4, 5, and 6 hours after administration. Resulting plasma salmon calcitonin for each dose and for each monkey is determined by radio-immunoassay.

For each monkey, the primate plasma salmon calcitonin (SCt) for one batch and one time period, mean plasma SCt concentrations for all monkeys for one batch and one time period, Standard Deviation (SD) of plasma SCt concentrations for one batch and one time period, and Standard Error of the Mean (SEM) for plasma SCt concentrations for all monkeys for one batch and one time period are calculated and reported in FIG. 5.

The invention claimed is:

1. An oral pharmaceutical composition in compressed tablet form comprising:
   i. parathyroid hormone (PTH) or a fragment thereof comprising at least amino acids 1 to 28 in an amount of about 1 µg/kg to about 6 µg/kg body weight:
   ii. N-(5-chlorosalicyloyl)-8-aminocaprylic acid (5-CNAC) in an amount of between 40 wt % and 60 wt % as delivery agent;
   (iii) crospovidone as a disintegrant in an amount of from 1.0 wt % to 8 wt %; and
   (iv) Avicel as a diluent in an amount of from 20 wt % to 70 wt %;
   wherein the composition has a disintegration time of no more than 6 minutes and a dissolution of >90% at 20 minutes and wherein the tablet has a hardness of between 3 Kp and 20 Kp.

2. The composition of claim 1, wherein the composition has a disintegration time of no more than 2 minutes.

3. The pharmaceutical composition of claim 1, wherein the tablet has a hardness of between 5 Kp and 15 Kp.

4. The pharmaceutical composition of claim 1, wherein the tablet has a disintegration time of less than 1 minute and a hardness of between 5 Kp and 7 Kp.

5. The composition of claim 1, wherein the PTH is PTH 1-34.

6. A method of manufacturing an oral pharmaceutical composition in compressed tablet form comprising the steps:
   i. blending parathyroid hormone (PTH) or a fragment thereof comprising at least amino acids 1 to 28 in an amount of about 1 µg/kg to about 6 µg/kg body weight with N-(5-chlorosalicyloyl)-8-aminocaprylic acid (5-CNAC) in an amount of between 40 wt % and 60 wt %, crospovidone in an amount of from 1.0 wt % to 8 wt %, and Avicel in an amount of from 20 wt % to 70 wt % to make a blend; and
   ii. compressing the blend into a tablet having a hardness of between 3 Kp and 20 Kp, wherein the composition has a disintegration time of no more than 6 minutes and a dissolution of >90% at 20 minutes.

7. The composition of claim 1 wherein the tablet does not include an enteric coating.

8. The composition of claim 7 wherein the tablet does not include a peptidase inhibitor.

* * * * *